(12) United States Patent
Hussam (10) Patent No.: US 8,762,170 B2
(45) Date of Patent: Jun. 24, 2014

(54) PATIENT PORTAL

(71) Applicant: Universal Research Solutions, LLC, Columbia, MO (US)

(72) Inventor: Ali Adel Hussam, Columbia, MO (US)

(73) Assignee: Universal Research Solutions, LLC, Columbia, MO (US)

( * ) Notice: Subject to any disclaimer, the term of this patent is extended or adjusted under 35 U.S.C. 154(b) by 0 days.

(21) Appl. No.: 14/104,349

(22) Filed: Dec. 12, 2013

(65) Prior Publication Data

US 2014/0100887 A1 Apr. 10, 2014

Related U.S. Application Data

(63) Continuation of application No. 13/181,461, filed on Jul. 12, 2011, now Pat. No. 8,630,870.

(51) Int. Cl.
*G06Q 50/00* (2012.01)
*G06Q 50/22* (2012.01)
*G06F 19/00* (2011.01)

(52) U.S. Cl.
CPC .............. *G06Q 50/22* (2013.01); *G06F 19/327* (2013.01); *G06F 19/322* (2013.01)
USPC .................................................. 705/2; 705/3

(58) Field of Classification Search
USPC ............................................................. 705/3
See application file for complete search history.

(56) References Cited

U.S. PATENT DOCUMENTS

2007/0273517 A1* 11/2007 Govind ...................... 340/572.1
2010/0076786 A1* 3/2010 Dalton et al. ..................... 705/3

OTHER PUBLICATIONS

Office Action in corresponding U.S. Appl. No. 13/181,461, dated Apr. 25, 2013, pp. 1-15.
Response to Office Action in corresponding U.S. Appl. No. 13/181,461, dated Jul. 23, 2013, pp. 1-24.
Final Office Action in corresponding U.S. Appl. No. 13/181,461, dated Aug. 16, 2013, pp. 1-13.
Response to Final Office Action in corresponding U.S. Appl. No. 13/181,461, dated Oct. 31, 2013, pp. 1-25.

* cited by examiner

*Primary Examiner* — John Pauls
*Assistant Examiner* — Jason Tiedeman
(74) *Attorney, Agent, or Firm* — Fish & Richardson P.C.

(57) ABSTRACT

A computer-implemented includes receiving, from one or more contributing channels, medical data; assigning the received medical data to one or more data silos; and generating a graphical user interface that when rendered on a display device renders a visual representation of a patient portal, with the patient portal including: one or more visual representations of the one or more data silos for data associated with a user that requested the patient portal.

29 Claims, 9 Drawing Sheets

PATIENT PORTAL

CLAIM OF PRIORITY

This application is a continuation of and claims priority under 35 U.S.C. §120 to U.S. application Ser. No. 13/181,461, which was filed Jul. 12, 2011, the entire contents of which are hereby incorporated by reference.

BACKGROUND

An electronic medical record ("EMR") is a computerized medical record created in an organization that delivers care, such as a hospital and/or a doctor's office. EMRs may be a part of a local stand-alone health data system that allows storage, retrieval and modification of records.

SUMMARY

In one aspect of the present disclosure, a computer-implemented method includes receiving, from one or more contributing channels, medical data; assigning the received medical data to one or more data silos; and generating a graphical user interface that when rendered on a display device renders a visual representation of a patient portal, with the patient portal including: one or more visual representations of the one or more data silos for data associated with a user that requested the patient portal.

Implementations of the disclosure may include one or more of the following features. In some implementations, the method includes receiving a request for the patient portal; and identifying, from the request, an identity of the user requesting the patient portal. In other implementations, the method includes querying, at least partly based on the identity of the user, the one or more data silos for medical data associated with the user. In still other implementations, the method includes receiving, based on querying, data associated with the user that requested the patient portal, and wherein the one or more visual representations of the one or more data silos include one or more visual representations of the received data.

In some implementations, the one or more data silos are configured to store a particular type of medical data for a plurality of users. In still implementations, the method includes parsing the received medical data; identifying, based on parsing, one or more types of medical data in the received medical data; for at least one of the identified types of medical data, determining a data silo configured to store the identified type of medical data; and assigning to the determined data silo the at least one identified type of medical data. In still other implementations, the graphical user interface dynamically displays the data silos and is generated in real-time. In some implementations, the method includes performing one or more pre-processing operations on the received medical data, wherein the one or more pre-processing operations include one or more of: using the received medical data in generating one or more discrete data elements; or indexing the received medical data in a search engine.

In another aspect of the disclosure, one or more machine-readable media are configured to store instructions that are executable by one or more processing devices to perform operations including receiving, from one or more contributing channels, medical data; assigning the received medical data to one or more data silos; and generating a graphical user interface that when rendered on a display device renders a visual representation of a patient portal, with the patient portal including: one or more visual representations of the one or more data silos for data associated with a user that requested the patient portal. Implementations of this aspect of the present disclosure can include one or more of the foregoing features.

In still another aspect of the disclosure, an electronic system includes one or more processing devices; and one or more machine-readable media configured to store instructions that are executable by the one or more processing devices to perform operations including: receiving, from one or more contributing channels, medical data; assigning the received medical data to one or more data silos; and generating a graphical user interface that when rendered on a display device renders a visual representation of a patient portal, with the patient portal including: one or more visual representations of the one or more data silos for data associated with a user that requested the patient portal. Implementations of this aspect of the present disclosure can include one or more of the foregoing features.

All or part of the foregoing may be implemented as a computer program product including instructions that are stored on one or more non-transitory machine-readable storage media, and that are executable on one or more processing devices. All or part of the foregoing may be implemented as an apparatus, method, or electronic system that may include one or more processing devices and memory to store executable instructions to implement the stated functions.

The details of one or more implementations are set forth in the accompanying drawings and the description below. Other features, objects, and advantages will be apparent from the description and drawings, and from the claims.

DETAILED DESCRIPTION

Described herein is a system for generating a patient portal to allow a patient to access different types of medical data that is related to the patient. Generally, a patient portal includes a graphical user interface that when rendered on a display device allows a patient (and/or any other user of the system) to access and to view data. For example, though the patient portal, the patient may access registration data, appointment data, medical form data, feedback data, education data, and outcome data. The system receives the various types of medical data related to the patient from different data sources, entities and/or channels that contribute medical data to the system. These numerous, different data sources, entities and/or channels are collectively referred to herein as "contributing channels," without limitation, for purposes of convenience.

Figure 1:
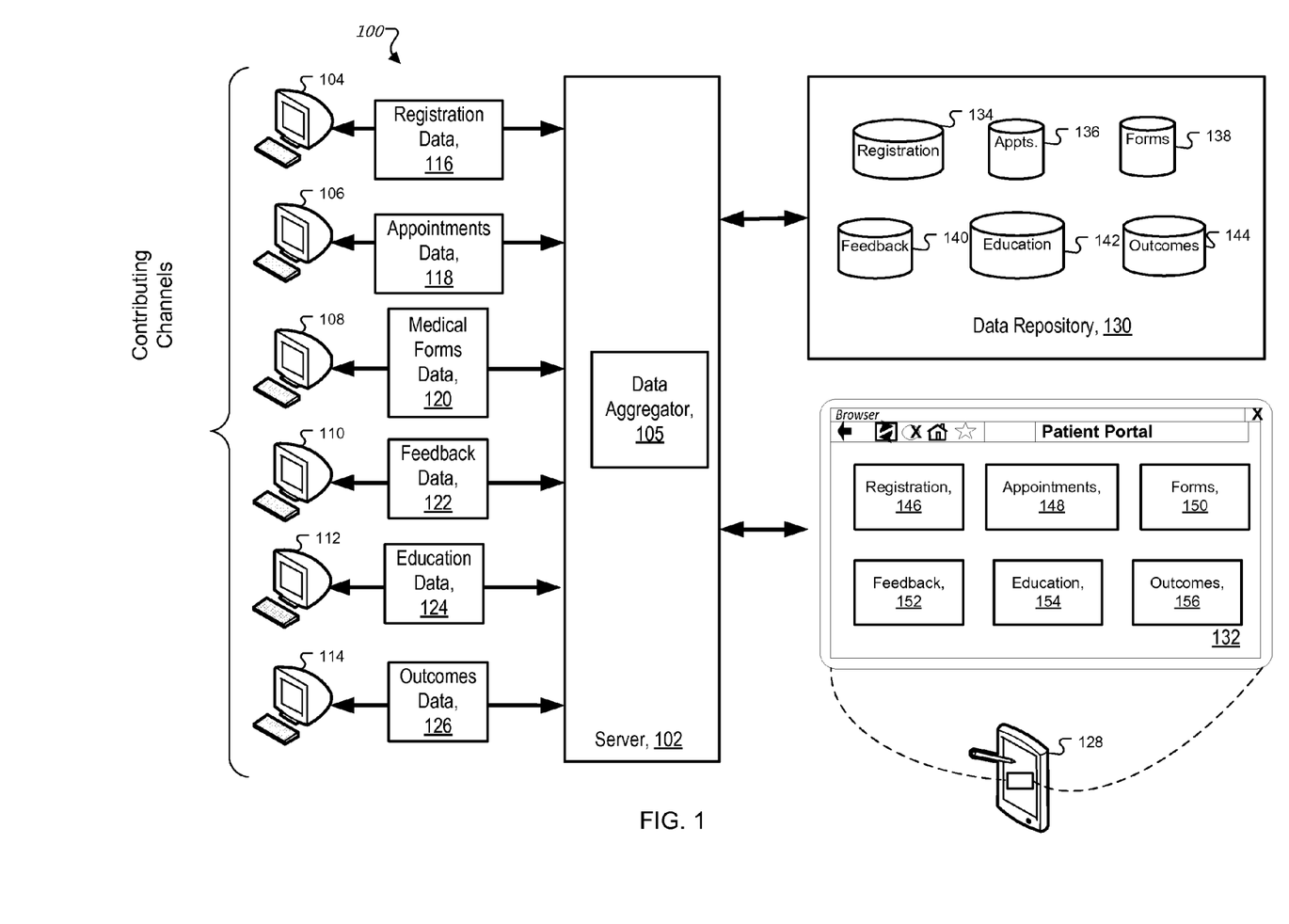
FIG. 1 is a conceptual diagram of a system for generating a patient portal.

FIG. 1 illustrates a particular exemplary embodiment describe herein. In particular, FIG. 1 is a conceptual diagram of system 100 for generating a patient portal. System 100 includes server 102. Server 102 includes data aggregator 105. In the illustrative example of FIG. 1, data aggregator is configured to receive contributing channel data from numerous contributing channels. In an example, contributing channel data includes, without limitation, registration data 116, appointment data 118, medical forms data 120, feedback data 122, education data 124, and outcome data 126.

In the illustrative example of FIG. 1, contributing channels include client devices 104, 106, 108, 110, 112, 114. In an exemplary embodiment, client device 104 is a device that sends registration data 116 to data aggregator 105. In this example registration data may include data pertaining to a patient's registration within a healthcare facility, a hospital, a clinic, and so forth. In the example of FIG. 1, registration data 116 does not have to be for a particular patient. Rather registration data 116 could be for a number of patients. That is, registration data 116 could be a stream of data that is received by data aggregator 105. Data aggregator 105 receives registration data 116 and parses registration data 116 to associate registration data 116 with various patients.

In an exemplary embodiment described herein, another contributing channel sends appointment data 118 to data aggregator 105. In particular, appointment data 118 may be sent by client device 106 which may include a computing device configured to store data pertaining to medical appointments. As described above with regard to registration data 116, appointment data 118 may pertain to a single patient or may pertain to a number of patients. In particular, appointment data 118 may be a stream of data combining medical appointment data for a plurality of patients.

Another contributing channel sends medical forms data 120. In the illustrative example of FIG. 1, medical forms data 120 is sent to data aggregator 105 by client device 108.

In this example, client device 108 may be a device that is configured to store medical forms, for example, as described in U.S. application Ser. No. 12/699,522, the entire contents of which are incorporated herein by reference. Another contributing channel sends feedback data 122. In this example, feedback data 122 may be sent to data aggregator 105 by user device 110. In this example, user device 110 is a device that is configured to collect from a patient feedback data, for example, as described in U.S. application Ser. No. 13/069,353, the entire contents of which are incorporated herein by reference. For example, feedback data is indicative of patient satisfaction with a medical procedure, a medical facility with a particular doctor and/or with particular medical staff.

Another type of contributing channel sends education data 124. In the illustrative example of FIG. 1, education data 124 is sent from the client device 112 to data aggregator 105. In this example, education data 124 includes data that is meant to educate a patient about a particular medical condition, a particular medical procedure, symptoms of a particular medical condition, allergic reactions, particular types of medication, and so forth.

Another type of contributing channel data that is received by data aggregator 105 is outcome data 126. In the illustrative example of FIG. 1, outcome data 126 is sent by client device 114 to data aggregator 105. In this example, client device 114 may include a system that is configured to receive data indicative of an outcome of a medical procedure, of medication and/or of a medical study as described in U.S. application Ser. No. 13/046,028, the entire contents of which are incorporated herein by reference. In the illustrative example of FIG. 1, data aggregator 105 receives outcome data 126 and stores outcome data 126.

Still referring to FIG. 1, data aggregator 105 receives contributing channel data from the various contributing channels 104, 106, 108, 110, 112, 114. Data aggregator 105 stores the contributing channel data that is received from the various contributing channels 104, 106, 108, 110, 112, 114. In an example, data aggregator 105 stores the contributing channel data in a manner that is compliant with the Health Insurance Portability and Accountability Act ("HIPPA"), secure, encrypted, and protected (e.g., protected health information ("PHI")). Data aggregator 105 may be configured to store the contributing channel data received from the contributing channels 104, 106, 108, 110, 112, 114 by a type of contributing channel data. For example, registration data 116 may be stored with other registration data. Appointment data 118 may be stored with other appointment data. Medical forms data 120 may be stored with other medical forms data and so forth.

In another example, data aggregator 105 may be configured to receive the contributing channel data from the various contributing channels 104, 106, 108, 110, 112, 114, parse the data to identify associations between portions of the data and various patient, and tag the data with information identifying which portions of the data are associated with which patients. Generally, a tag includes a data container in which data is stored in accordance with a pre-defined standard. The process of associating data with a tag is commonly referred to as "tagging."

For example, registration data 116 may include data for two patients, namely, John Johnson and Sally Hayes. Appointment data 118 may also include data for these patients, John Johnson and Sally Hayes. In this example, data aggregator 105 is configured to parse registration data 116 to identify the portion of registration data 116 that is for John Johnson and to also identify the other portion of registration data 116 that is for Sally Hayes.

Once data aggregator 105 has identified the portions of registration data 116 that are for John Johnson and Sally Hayes, respectively, data aggregator 105 is configured to tag this data accordingly such that the tag identifies an identity of the patient associated with the portions of registration data 116. For example, the portion of registration data 116 that is for John Johnson is tagged with data specifying a patient identity of John Johnson. Similarly, the portion of registration data 116 that is tagged for Sally Hayes is associated with data specifying that this portion of registration data 116 is for Sally Hayes.

In another exemplary embodiment described herein, data aggregator 105 may also be configured to store numerous different types of contributing channel data on a per patient basis. For example, the contributing channel data for John Johnson may be collected and correlated together and stored in a portion of data repository 130 that is specific for John Johnson. Similarly, the contributing channel data for Sally Hayes may be collected and correlated together in an area of database 130 that is designated for Sally Hayes.

Still referring to FIG. 1, data repository 130 is configured to store contributing channel data received from the various contributing channels 104, 106, 108, 110, 112, 114 including, for example, registration data 116, appointment data 118, medical forms data 120, feedback data 122, education data 124, and outcome data 126.

In an example, data repository 130 is configured to store contributing channel data in various data structures, including, e.g., silo data structures ("silos"). Generally, a silo includes a data structure that provides storage and/or access to a particular type of data. Data repository 130 includes numerous silos including, for example, silo 134, silo 136, silo 138, silo 140, silo 142, silo 144. In this example, data repository 130 includes a silo for each type of contributing channel. That is, data repository 130 includes a correspondence between a silo and a type of contributing channel. Accordingly, in the exemplary embodiment of FIG. 1, silo 134 stores registration data 116. Similarly, silo 136 stores appointments data 118. Silo 138 stores medical forms data 120. Silo 140 stores feedback data 122. Silo 142 stores education data 124. Silo 144 stores outcome data 126.

In the illustrative example of FIG. 1, silos 134, 136, 138, 140, 142, 144 may be configured to store medical data for a plurality of patients. For example, silo 134 may be configured to store registration data 116 for both John Johnson and Sally Hayes. In a variation of FIG. 1, data repository 130 may include silos that are specific for particular patients and/or for particular types of contributing channel data. For example, data repository 130 may include a silo (not shown) for registration data 116 for John Johnson. Data repository 130 may also include different silo (not shown) for registration data 116 for Sally Hayes.

In still another variation of FIG. 1, data repository 130 may be configured to store silos including numerous, different types of contributing channel data for a patient. For example, data repository 130 may include a silo that includes registration data 116, appointment data 118, medical forms data 120, feedback data 122, education data 124, and outcome data 126 for John Johnson. Data repository 130 may include another different silo that includes registration data 116, appointment data 118, medical forms data 120, feedback data 122, education data 124, and outcome data 126 for Sally Hayes.

Still referring to FIG. 1, system 100 includes another client device, namely, client device 128. In this example, client device 128 is used by a patient to access patient portal 132. As illustrated in FIG. 1, data aggregator 105 generates patient portal 132 which may be, for example, a graphical user interface that when rendered on client device 128 renders visual representations of silos 134, 136, 138, 140, 142, 144. In particular, visual representations of the foregoing silos may be represented as virtual silos, including, for example, virtual silo 146, virtual silo 148, virtual silo 150, virtual silo 152, virtual silo 154, and virtual silo 156.

In the illustrative example of FIG. 1, virtual silo 146 pertains to registration data 116 and provides the user with a visual representation of silo 134. That is, virtual silo 146 corresponds to silo 134. Similarly, virtual silo 148 pertains to appointment data 118 and provides the user with a visual representation of silo 136. Virtual silos 150, 152, 154 and 156 each provide a user with visual representations of their respective silos in data repository 130.

In the illustrative example of FIG. 1, graphical user interface 132 displays data that is for a particular patient. That is, virtual silos 146, 148, 150, 152, 154, 156 display data that is particular to a specific patient. In this example, silos 134, 136, 138, 140, 142, 144 are silos that include contributing channel data for numerous patients including, for example, John Johnson and Sally Hayes in the foregoing example. Because silos 134, 136, 138, 140, 142, 144 include a particular type of contributing channel data for numerous patients, data aggregator 105 is configured to query each of these silos 134, 136, 138, 140, 142, 144 to obtain data that corresponds to the patient that is requesting patient portal 132.

For example, the user of client device 128 may be John Johnson. In this example, John Johnson accesses patient portal 132. To provide John Johnson access to patient portal 132, data aggregator 105 generates a graphical user interface that renders a visual representation of patient portal 132. In generating virtual silos 146, 148, 150, 152, 154, 156, data aggregator 105 queries silos 134, 136, 138, 140, 142, 144 for data associated and/or tagged with data specifying a patient name of John Johnson. Once data aggregator 105 has identified this data in the various silos 134, 136, 138, 140, 142, 144, data aggregator 105 is able to select this data from the various silos 134, 136, 138, 140, 142, 144 and make this data accessible through virtual silos 146, 148, 150, 152, 154, 156 in patient portal 132.

Figure 2:
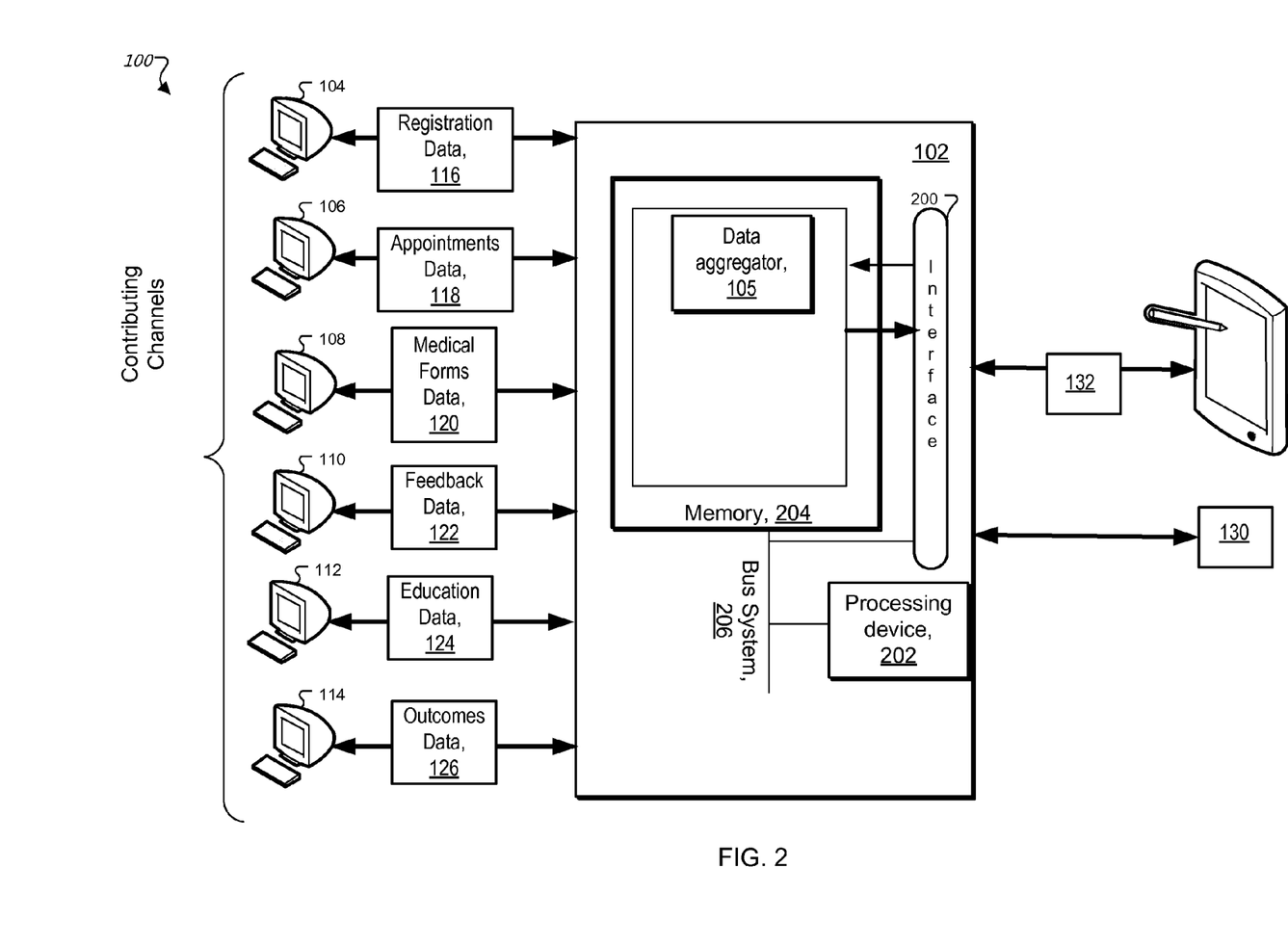
FIG. 2 is a block diagram of components of the system for generating a patient portal.

FIG. 2 illustrates a particular exemplary embodiment describe herein. FIG. 2 is a block diagram of components of system 100 for generating a patient portal.

Client devices 104, 106, 108, 110, 112, 114, 128 can be any sort of computing devices capable of taking input from a user and communicating over a network (not shown) with server 102 and/or with other client devices. For example, client devices 104, 106, 108, 110, 112, 114, 128 can be mobile devices, desktop computers, laptops, cell phones, personal digital assistants ("PDAs"), servers, embedded computing systems, and so forth.

In the exemplary embodiment of FIG. 2, server 102 can be any of a variety of computing devices capable of receiving data, such as a server, a distributed computing system, a desktop computer, a laptop, a cell phone, a rack-mounted server, and so forth. Server 102 may be a single server or a group of servers that are at a same location or at different locations.

The illustrated server 102 can receive data from client devices 104, 106, 108, 110, 112, 114, 128 via input/output ("I/O") interface 200. I/O interface 200 can be any type of interface capable of receiving data over a network, such as an Ethernet interface, a wireless networking interface, a fiber-optic networking interface, a modem, and so forth. Server 102 also includes a processing device 202 and memory 204. A bus system 206, including, for example, a data bus and a motherboard, can be used to establish and to control data communication between the components of server 102.

The illustrated processing device 202 may include one or more microprocessors. Generally, processing device 202 may include any appropriate processor and/or logic that is capable of receiving and storing data, and of communicating over a network (not shown). Memory 204 can include a hard drive and a random access memory storage device, such as a dynamic random access memory, or other types of non-transitory machine-readable storage devices. As shown in FIG. 2, memory 204 stores computer programs that are executable by processing device 202. Among these computer programs is data aggregator 105.

Memory 204 is also configured to execute a processing engine (not shown). The processing engine is configured to perform pre-processing operations to prepare contributing channel data for processing by data aggregator 105 and/or to prepare data for processing and generating as cross-channel data, e.g., which is described in U.S. Ser. No. 13/159,155, the contents of which are incorporated herein by reference. As described in further detail below, the pre-processing operations include search engine indexing operations and generation of discrete data elements operations.

In another example, the processing engine may execute on client devices 104, 106, 108, 110, 112, 114, e.g., rather than or in addition to executing on server 110. In this example, a client device executes the processing engine to prepare contributing channel data for transfer to server 110. The processing engine uses data stored on the client device and/or retrieved by the client device and generates discrete data elements that may be transferred to server 110. That is, after the processing engine of the client device has generated the discrete data elements, the processing engine may contribute (e.g., transfer) the discrete data elements to data aggregator 105.

In an example, the processing engine receives data and generates discrete data elements by using a data filter to format data from a first data format to a second data format, for example, as described in U.S. Ser. No. 12/774,694, the entire contents of which are incorporated herein by reference. In still another example, the processing engine generates the discrete data elements by performing optical character recognition ("OCR") on the contributing channel data.

In still another example, the processing engine (e.g., executing on a client device and/or on server 110) includes a search component (e.g., a search engine). The search component indexes the contributing channel data, e.g., that is stored in data repository 130, for example using indexing techniques that are well known in the art. In this example, the search component includes a spider (e.g., a web traversal portion of a search engine) that collects contributing channel data (e.g., discrete data elements) for indexing in data repository 130, e.g., as is commonly known in the art.

Through the search component, a user may search data repository 130 for a particular type of data (e.g., discrete data elements) and/or for data received from a particular type of contributing entity and/or for historic, live data, and so forth. In an example, a user may access the search component to search for patients having particular conditions. In another example, the user may access the search component to search for patients associated with particular medical codes and/or medical forms. In still another example, data aggregator 105 performs OCR on the received contributing channel data. In this example, the user may perform word searches in identifying different types of data.

Figure 3A:
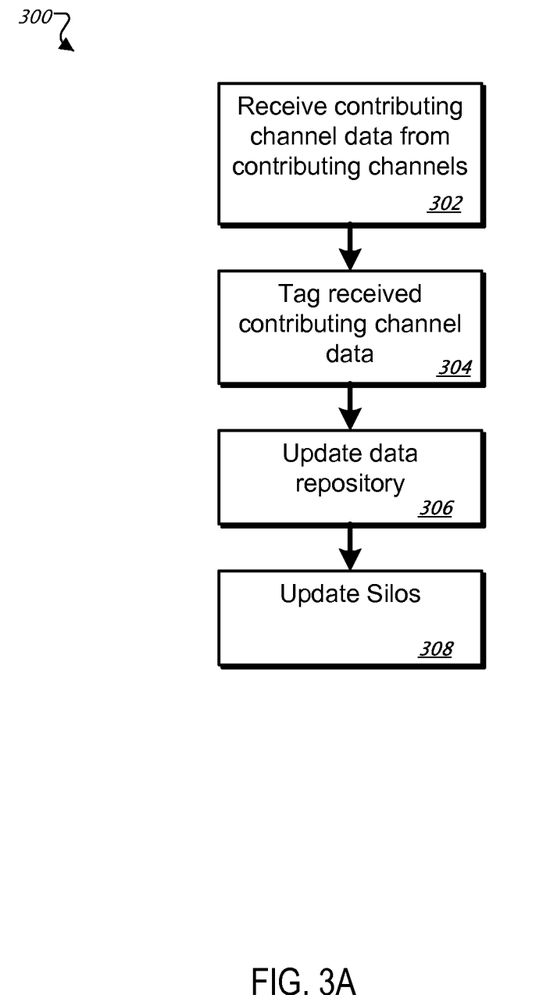
FIG. 3A is a flow chart of a process for updating a data repository with contributing channel data.

FIG. 3A illustrates a particular exemplary embodiment describe herein. In particular, FIG. 3A is a flow chart of process 300 for updating data repository 130 with contributing channel data 116, 118, 120, 122, 124, 126. In operation, data aggregator 105 receives contributing channel data 116, 118, 120, 122, 124, 126 from contributing channels 104, 106, 108, 110, 112, 114. Data aggregator 105 tags (304) the received contributing channel data 116, 118, 120, 122, 124, 126 with a patient identifier identifying the patient associated with the received contributing channel data 116, 118, 120, 122, 124, 126.

For example, portions of the received contributing channel data 116, 118, 120, 122, 124, 126 include patient identifying information. Data aggregator 105 parses the received contributing channel data 116, 118, 120, 122, 124, 126 to identify the patient identifying information and to identify which portions of the received contributing channel data 116, 118, 120, 122, 124, 126 are associated with which portions of the patient identifying information. Using the correspondence between portion of the patient identifying information and other portions of the received contributing channel data 116, 118, 120, 122, 124, 126, data aggregator 105 tags the received contributing channel data 116, 118, 120, 122, 124, 126 with information specifying a correspondence between portions of the received contributing channel data 116, 118, 120, 122, 124, 126 and various patients.

Still referring to FIG. 3A, data aggregator 105 updates (306) data repository 130 with the received contributing channel data 116, 118, 120, 122, 124, 126. In the illustrative example of FIG. 1, where the received contributing channel data 116, 118, 120, 122, 124, 126 is stored in silos 134, 136, 138, 140, 142, 144, data aggregator 105 updates (308) silos 134, 136, 138, 140, 142 and 144 with the received contributing channel data 116, 118, 120, 122, 124, 126, which may be tagged as described in the foregoing example. For example, data aggregator 105 may determine which silo corresponds to a particular type of contributing channel data and update that silo by storing the received contributing channel data for that particular type in the appropriate silo. For example, received registration data 116 is stored (e.g., in real-time and automatically) in an appropriate silo, namely, silo 134, at least because silo 134 is configured to store registration data 116.

Figure 3B:
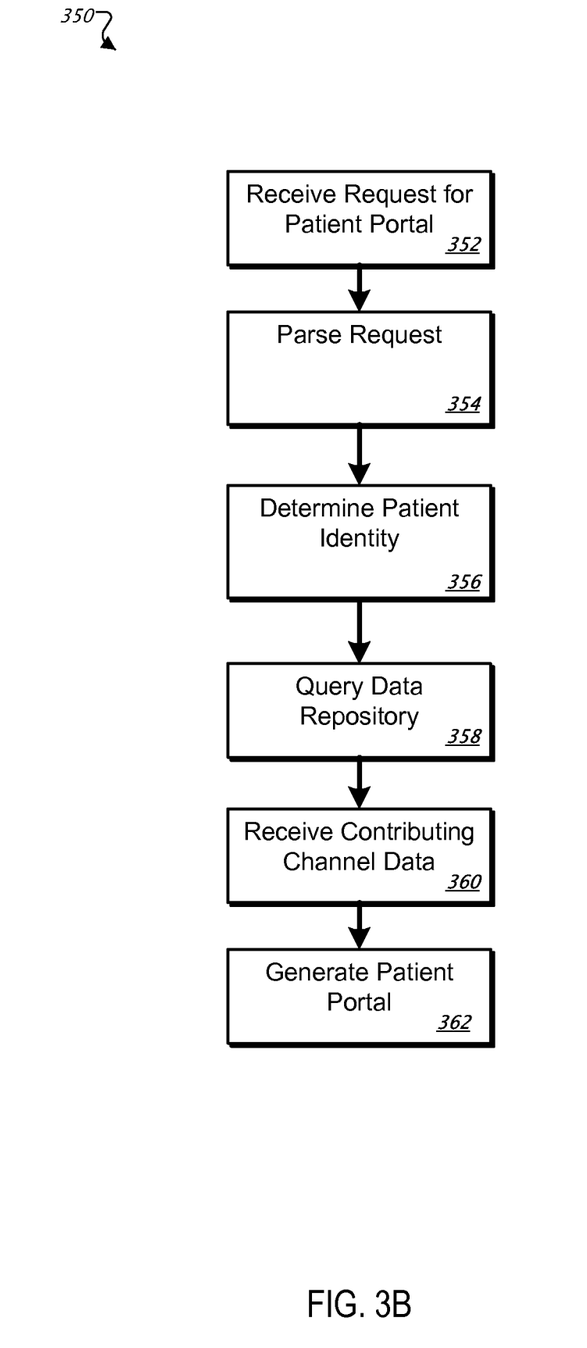
FIG. 3B is a flow chart of a process for generating a patient portal.

FIG. 3B illustrates a particular exemplary embodiment describe herein. In particular, FIG. 3B is a flow chart of process 350 for generating patient portal 132. In operation, data aggregator 105 receives (352) a request for patient portal 132, for example, by a user accessing a website that is associated with the patient portal and/or logging into a website that is associated with the patient portal. In response, data aggregator 105 parses (354) the request for patient portal 132. Using the results of parsing, data aggregator 105 determines (356) the patient identity of the patient that has requested the patient portal, for example, based on the user name and password information that the user used to log into the website. Data aggregator 105 queries (358) data repository 130 for contributing channel data associated with the identified patient. In particular, the data aggregator 105 may query silos 134, 136, 138, 140, 142, 144 for data associated with the patient that has requested patient portal 132.

In this example, data aggregator 105 determines from the request the name of the patient that has requested patient portal 132. Data aggregator 105 queries silos 134, 136, 138, 140, 142, 144 for data associated with the same patient name that was included in the request. In this example, silos 134, 136, 138, 140, 142, 144 may include tables of data with a portion of the table including the contributing channel data and with the other portion of the table associating the contributing channel data with a patient identifier, for example, the name of the patient. In this example, data aggregator 105 submits to silos 134, 136, 138, 140, 142, 144 the patient identifier. Using the patient identifier, data repository 130 determines contributing channel data that is tagged with information corresponding to the patient identifier and/or contributing channel data that is otherwise associated with the patient identifier (e.g., through the foregoing table).

Still referring to FIG. 3B, data aggregator 105 receives (360) from data repository 130 appropriate contributing channel data for the user requesting patient portal 132. Using the received contributing channel data, data aggregator 105 generates (362) patient portal 132, as described herein, for example, by generating virtual silos for each type of received contributing channel data (e.g., virtual silos 146, 148, 150, 152, 154, 156).

Figure 4:
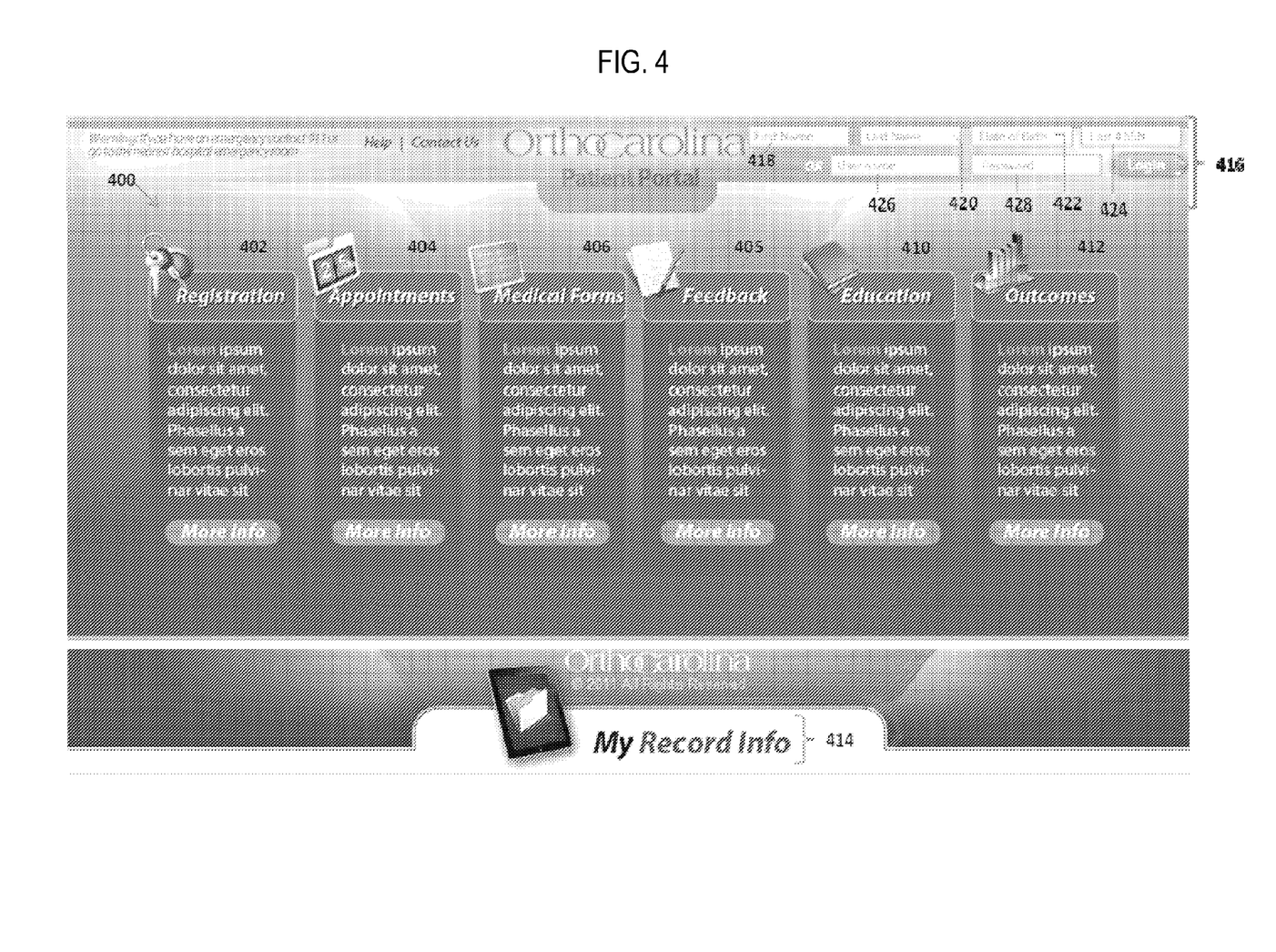
FIGS. 4-8 are example graphical user interfaces included in a patient portal. Like reference symbols in the various drawings indicate like elements.

FIG. 4 illustrates a particular exemplary embodiment describe herein. In particular, FIG. 4 is an example of graphical user interface 400 included in patient portal 132. In the illustrative example of FIG. 4, data aggregator 105 generates virtual silos 402, 404, 406, 408, 410, 412, including, e.g., visual representations of silos 134, 136, 138, 140, 142, 144. In an example, data aggregator 105 is configured to dynamically and in real-time update visual representations of silos 134, 136, 138, 140, 142, 144, for example, based on newly received contributing channel data.

In the illustrative example of FIG. 4, virtual silo 402 providers a user with registration data 116, including, e.g., names of medical facilities with which the user is currently registered, forms that may be used by the user to register at additional medical facilities, and so forth. Virtual silo 404 provides the user with appointment data 118, including, e.g., medical appointments that the user has scheduled and/or needs to schedule. Virtual silo 406 provides the user with medical forms data 120, including, e.g., medical questionnaires for the user to fill out prior to an appointment with a physician, medical assessment forms for the user to fill out assist a physician and/or automated medical assessment system in diagnosing an ailment of the user, and so forth.

Virtual silo 408 provides the user with feedback data 122, including, e.g., online forms through which the user can submit feedback for a particular medical professional, medical facility, medical procedure, and so forth. Virtual silo 410 provides the user with education data 124, including, e.g., data pertaining to a physical ailment of the patient, data describing medical conditions, data describing various side-effects of a medication, and so forth. Virtual silo 412 provides the user with outcome data 126, including, e.g., data indicative of the outcome a medical procedure, such as whether the procedure was a success and/or a failure.

Graphical user interface 400 also includes portion 414 through which a user may access and view additional data that is specific to the user. In this illustrative example of FIG. 4, portion 414 includes a selectable link, selection of which causes data aggregator 105 to display the data that is specific to the user. Graphical user interface 400 also includes portion 416 for a user to login into patient portal 132. In an example, the user may log into the patient portal by entering into text boxes 418, 420, 422, 424 data identifying the user, including, e.g., first name data, last name data, date of birth data, and social security data. The user may also log into patient portal 132 via a user account that uniquely identifies the user. In the illustrative example of FIG. 4, the user enters the user account data into text boxes 426, 428.

Figure 5:
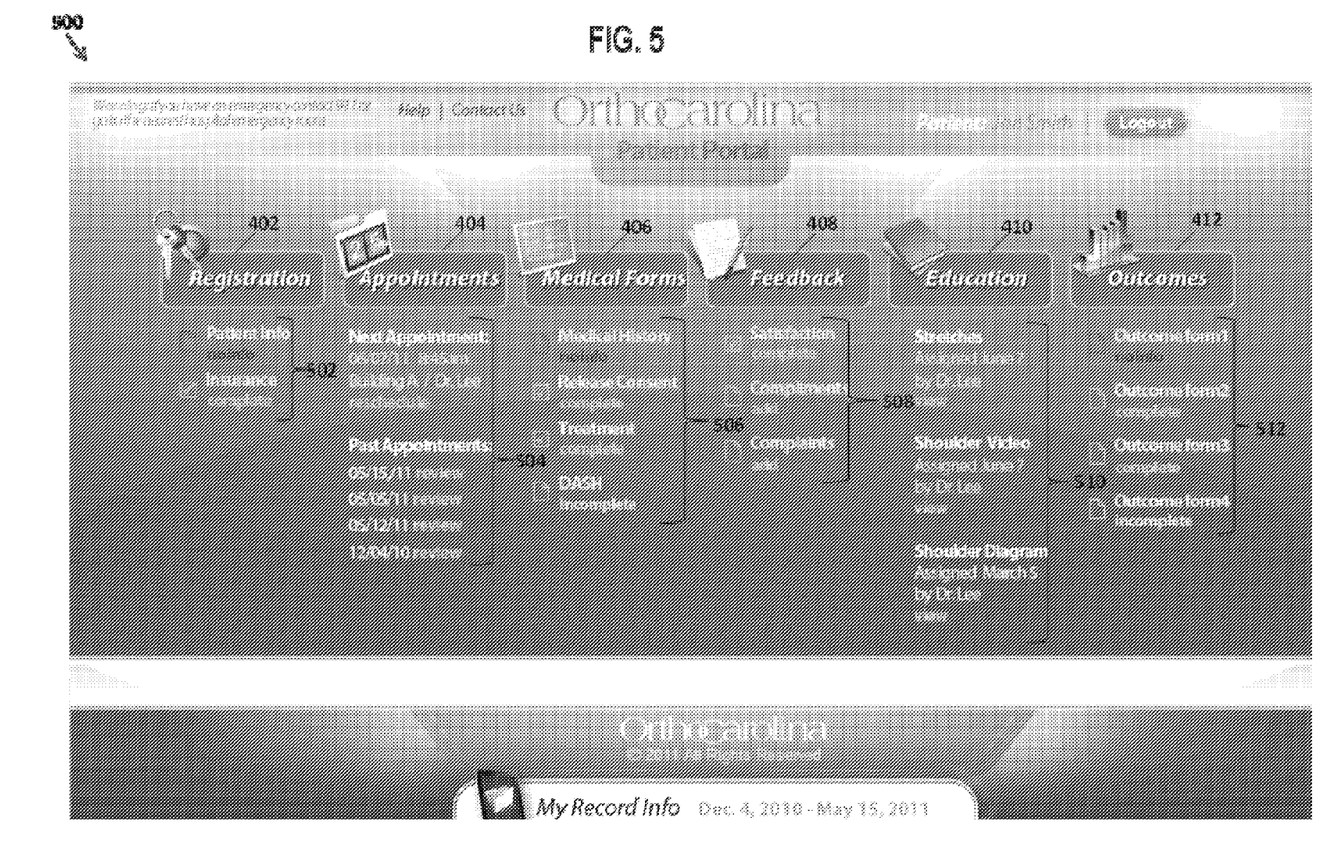

FIG. 5 illustrates a particular exemplary embodiment describe herein. In particular, FIG. 5 is an example of graphical user interface 500 included in the patient portal. In the illustrative example of FIG. 5, graphical user interface 500 is generated by data aggregator 105 after the user logs into the patient portal. After the user logs into the patient portal, data aggregator 105 retrieves contributing channel data 502, 504, 506, 508, 510, 512 (e.g., from silos 134, 136, 138, 140, 142, 144) that is associated with the user.

In an example, data aggregator 105 is configured to retrieve contributing channel data 502, 504, 506, 508, 510, 512 in real-time from silos 134, 136, 138, 140, 142, 144. In this example, data aggregator 105 sends real-time requests to data repository 130 for contributing channel data 502, 504, 506, 508, 510, 512, for example, when the user log into patient portal 132. In this example, data aggregator 105 sends the user's login information to data repository 130 to promote an ability of data repository 130 to identify contributing channel data that is specific to the user (e.g., by identifying contributing channel data that is tagged with data corresponding to the login information) and to send this contributing channel data to data aggregator 105.

In the illustrative example of FIG. 5, at least a portion of contributing channel data 502, 504, 506, 508, 510, 512 includes selectable data, selection of which allows the user to view and to access a particular item of contributing channel data. In an example, a particular item of contributing channel data is juxtaposed to a link, selection of which allows the user to view the particular item of contributing channel data. Generally, juxtaposition includes a placement of an item of data in proximity to another item of data. In another example, virtual silos 402, 404, 406, 408, 410, 412 includes selectable areas, selection of which enables a user to view data included in the selected silo.

Figure 6:
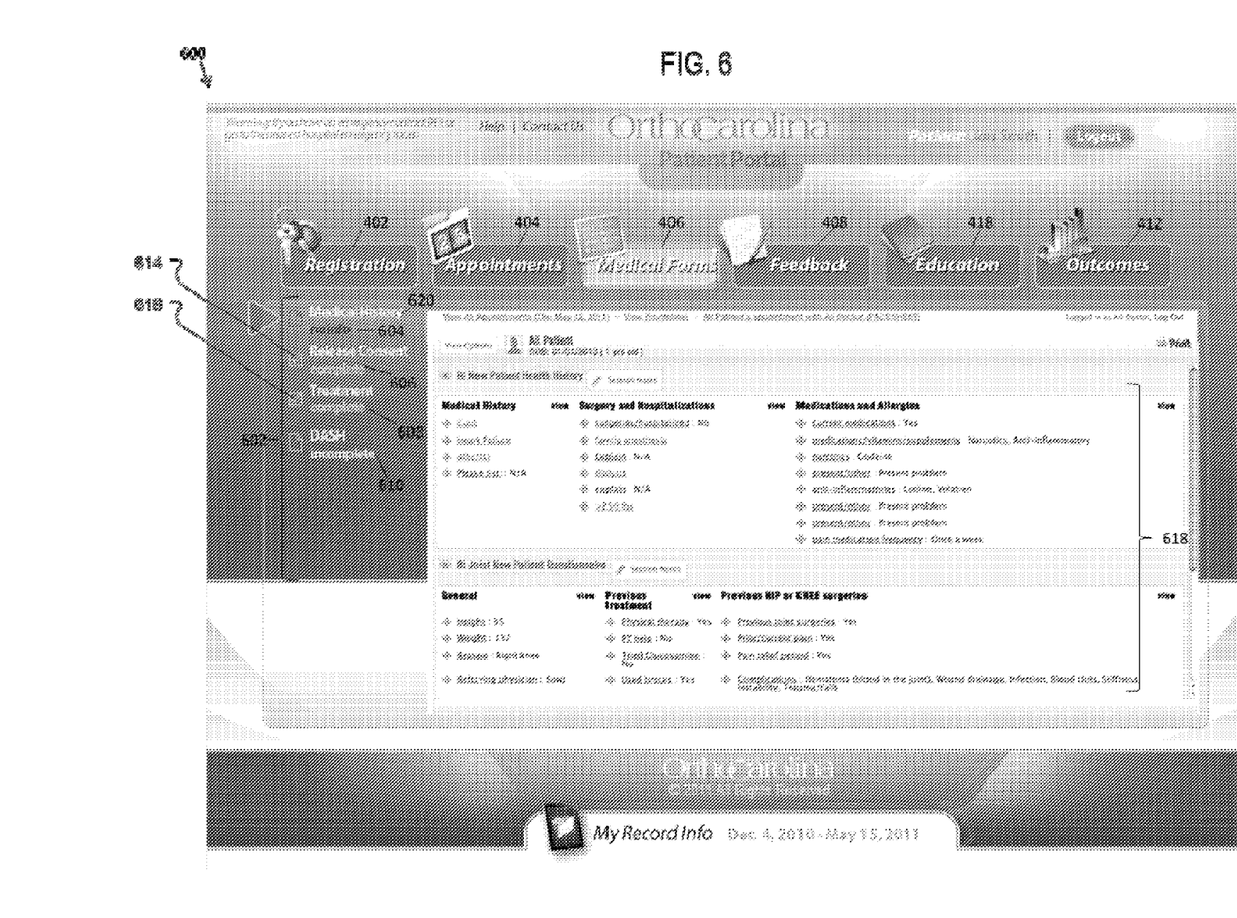

FIG. 6 illustrates a particular exemplary embodiment describe herein. In particular, FIG. 6 is an example of graphical user interface 600 included in patient portal. In the illustrative example of FIG. 6, the user has selected virtual silo 406 to view medical forms that are associated with the user.

In the illustrative example of FIG. 6, graphical user interface 600 includes menu area 602 that displays for the user the different types of medical forms that are associated with the user. Menu area 602 also includes data indicative of a completion status for each of the forms. In the illustrative example of FIG. 6, menu area 602 includes completion status indicators 604, 606, 608, 610. Completion status indicators 604, 606, 608, 610 provide the user with data specifying a status of a particular medical form, including, e.g., whether the medical form is complete, incomplete, and/or if no data has been provided for the medical form. In an example, visual representations 614, 616 are juxtaposed to completion status indicators 604, 606, 608, 610. Visual representations 614, 616 provide the user with a visual indicator (e.g., a check mark or other visual indicator) that a particular medical form has been completed by the user.

Graphical user interface 600 also includes portion 618 that provides the user with the contents of a selected form. In the illustrative example of FIG. 6, the user has selected medical history link 620. Accordingly, portion 618 is populated with data indicative of the medical history of the user.

Figure 7:
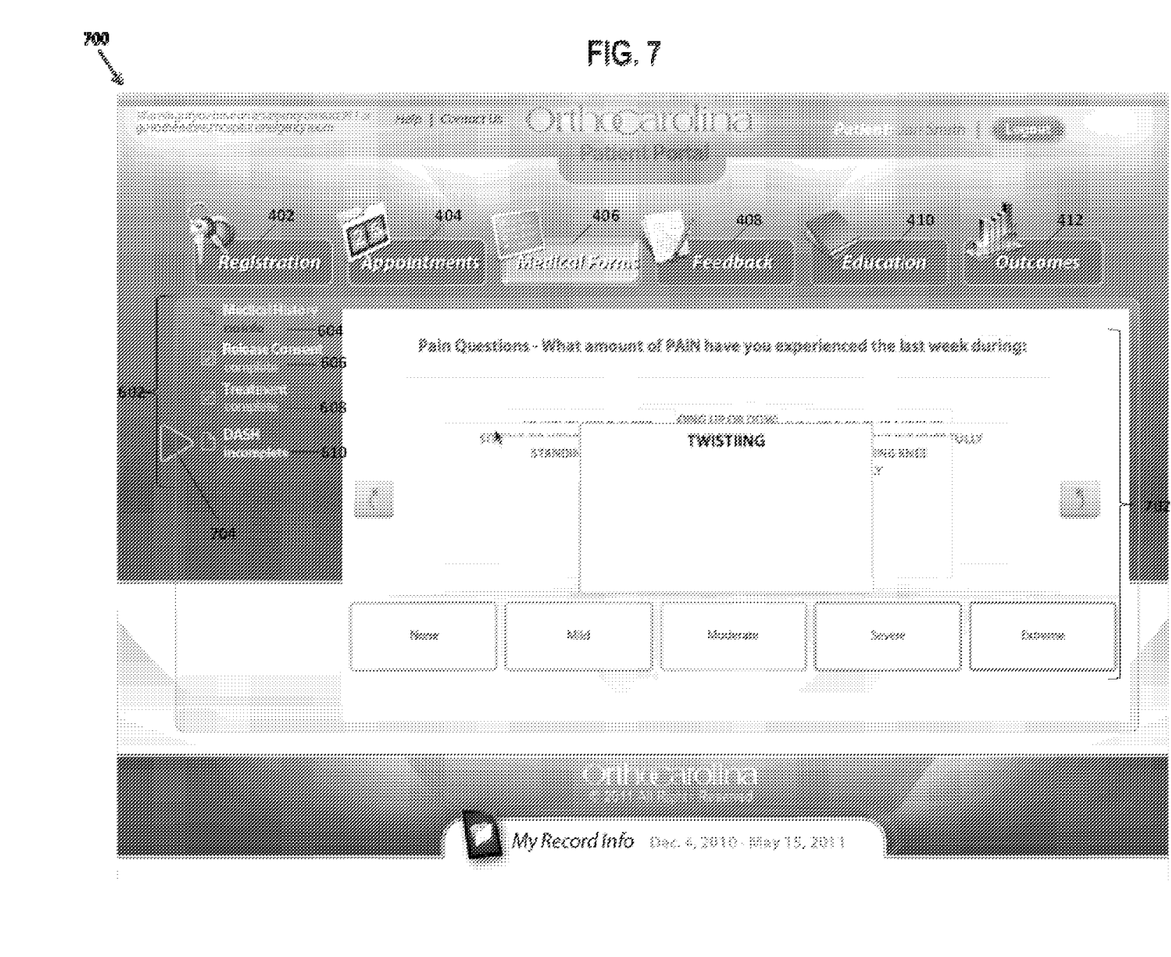

FIG. 7 illustrates a particular exemplary embodiment describe herein. In particular, FIG. 7 is an example of graphical user interface7 included in the patient portal. In FIG. 7, the user has selected another link in virtual silo 406. In the illustrative example of FIG. 7, the user has selected to view the dash form 704. In this example, selected medical form is incomplete, e.g., as indicated by completion status indicator 610. Accordingly, portion 702 is populated with contents of dash form 704 to assist the user in completing the form.

Figure 8:
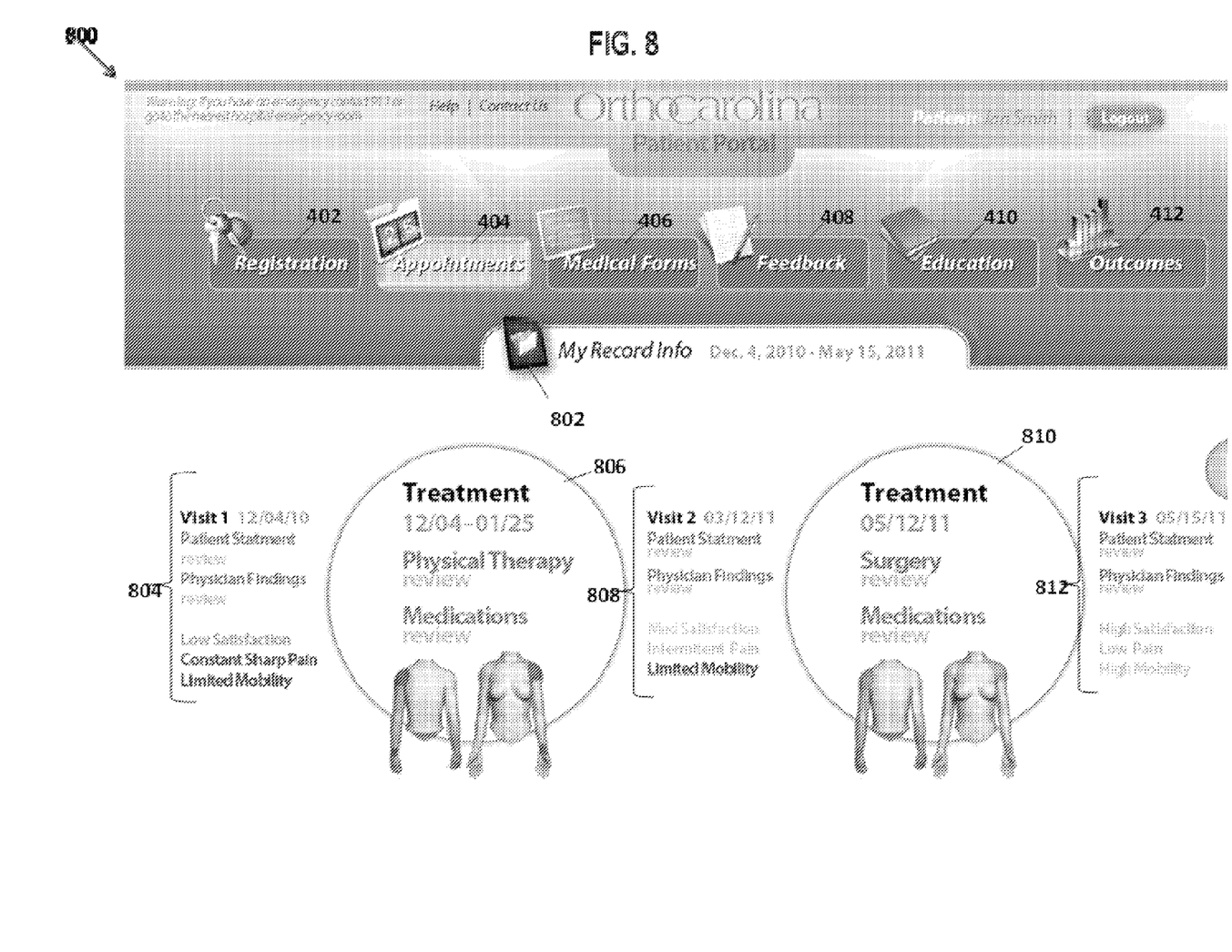

FIG. 8 illustrates a particular exemplary embodiment describe herein. In particular, FIG. 8 is an example of graphical user interface 800 included in patient portal 132. In the exemplary embodiment of FIG. 8, data aggregator 105 enables the patient to view physical notes and progress data, via, graphical user interface 800. In the illustrative example of FIG. 8, graphical user interface 800 includes virtual silos 402, 404, 406, 408, 410, 412. In the illustrative example of FIG. 8, the patient has selected area 802 to view the patient's personal records. The patient's personal record includes visual representation 804. Visual representation 804 includes a representation of the patient's first visit to a physician (and/or a medical facility), including a patient statement, the physician's findings, and the satisfaction level that has been indicated by the patient. Graphical user interface 800 also includes visual representation 806 which includes a visual representation of the dates of treatment for the patient (e.g., associated with the first visit) and an illustrative diagram of the areas of the patient's body in which the patient has received treatment.

Graphical user interface 800 also includes visual representation 808 that includes data indicative of a patient's second visit to the physician. Graphical user interface 800 also includes visual representation 810 including an additional visual representation of the treatment that the patient has received on a different date. Graphical user interface 800 also includes visual representation 812 including data indicative a patient's third visit to the physician.

In a variation of FIG. 8, a visual representation of trends over visits may be shown. Generally, trends over visits include information indicative of trends and/or progressions in patient health over a period of time and/or over a number of office visits. For example, if a patient has cholesterol measured each time the patient visits the physician, data aggregator 105 may be configured to generate a visual representation of the patient's cholesterol measurements over a period of time (e.g., for each of the office visits).

In still another configuration, data aggregator 105 is configured to identify stale data (e.g., in the silos) and to generate alerts to notify users of the stale data. Generally, stale data refers to data that is older than a predefined period of time. In an example, when a graphical user interface includes a visual representation of a silo, and that silo includes stale data, data aggregator 105 is configured to generate an alert to notify a viewer of the graphical user interface that at least a portion of the data is stale.

Data aggregator 105 is also configured to generate reminders (e.g., automated reminders) to notify users of the patient portal of upcoming appointments, of forms that need to be filled out and other tasks to be performed. In an example, users may set reminder dates for certain tasks and/or functionality that is provided through the patient portal.

Data aggregator 105 is also configured to provide semantic highlighting and semantic color coding for contributing channel data. For example, a particular type of contributing channel data may assigned a particular color (e.g., purple) and a different type of contributing channel data may be assigned another, different color (e.g., blue). The contributing channel is displayed in a graphical user interface in accordance with the assigned semantic color coding, e.g., to promote an ability of a user to visually identify certain types of contributing channel, e.g., based on the semantic color coding.

Embodiments can be implemented in digital electronic circuitry, or in computer hardware, firmware, software, or in combinations thereof. An apparatus can be implemented in a computer program product tangibly embodied or stored in a machine-readable storage device for execution by a programmable processor; and method actions can be performed by a programmable processor executing a program of instructions to perform functions by operating on input data and generating output. The embodiments described herein, and other embodiments of the invention, can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language.

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Computer readable media for embodying computer program instructions and data include all forms of non-volatile memory, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in special purpose logic circuitry. Any of the foregoing can be supplemented by, or incorporated in, ASICs (application-specific integrated circuits).

To provide for interaction with a user, embodiments can be implemented on a computer having a display device, e.g., a LCD (liquid crystal display) monitor, for displaying data to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments can be implemented in a computing system that includes a back end component, e.g., as a data server, or that includes a middleware component, e.g., an application server, or that includes a front end component, e.g., a client computer having a graphical user interface or a Web browser through which a user can interact with an implementation of embodiments, or any combination of such back end, middleware, or front end components. The components of the system can be interconnected by any form or medium of digital data communication, e.g., a communication network. Examples of communication networks include a local area network (LAN) and a wide area network (WAN), e.g., the Internet.

The system and method or parts thereof may use the "World Wide Web" (Web or WWW), which is that collection of servers on the Internet that utilize the Hypertext Transfer Protocol (HTTP). HTTP is a known application protocol that provides users access to resources, which may be data in different formats such as text, graphics, images, sound, video, Hypertext Markup Language (HTML), as well as programs. Upon specification of a link by the user, the client computer makes a TCP/IP request to a Web server and receives data, which may be another Web page that is formatted according to HTML. Users can also access other pages on the same or other servers by following instructions on the screen, entering certain data, or clicking on selected icons. It should also be noted that any type of selection device known to those skilled in the art, such as check boxes, drop-down boxes, and the like, may be used for embodiments using web pages to allow a user to select options for a given component. Servers run on a variety of platforms, including UNIX machines, although other platforms, such as Windows 2000/2003, Windows NT, Sun, Linux, and Macintosh may also be used. Computer users can view data available on servers or networks on the Web through the use of browsing software, such as Firefox, Netscape Navigator, Microsoft Internet Explorer, or Mosaic browsers. The computing system can include clients and servers. A client and server are generally remote from each other and typically interact through a communication network. The relationship of client and server arises by virtue of computer programs running on the respective computers and having a client-server relationship to each other.

Other embodiments are within the scope and spirit of the description claims. Additionally, due to the nature of software, functions described above can be implemented using software, hardware, firmware, hardwiring, or combinations of any of these. Features implementing functions may also be physically located at various positions, including being distributed such that portions of functions are implemented at different physical locations. The use of the term "a" herein and throughout the application is not used in a limiting manner and therefore is not meant to exclude a multiple meaning or a "one or more" meaning for the term "a." Additionally, to the extent priority is claimed to a provisional patent application, it should be understood that the provisional patent application is not limiting but includes examples of how the techniques described herein may be implemented.

A number of exemplary embodiments of the invention have been described. Nevertheless, it will be understood by one of ordinary skill in the art that various modifications may be made without departing from the spirit and scope of the invention.

What is claimed is:

1. A computer-implemented method comprising:
receiving, from a plurality of contributing organizations, medical form data for a patient, medical education data for the patient and medical outcome data for the patient;
aggregating the data received from the plurality of contributing organizations to generate aggregated medical form data for the patient, aggregated medical education data for the patient and aggregated medical outcome data for the patient; and
generating data for a graphical user interface that when rendered on a display device renders a visual representation of a patient portal, with the graphical user interface comprising one or more of:
a first portion that specifies that the aggregated medical form data for the patient is viewable through the patient portal, with selection of the first portion causing a display of the aggregated medical form data when the aggregated medical form data is available;
a second portion that specifies that the aggregated medical education data for the patient is viewable through the patient portal, with selection of the second portion causing a display of the aggregated medical education data when the aggregated medical education data is available; and
a third portion that specifies that the aggregated medical outcome data for the patient is viewable through the patient portal, with selection of the third portion causing a display of the aggregated medical outcome data when the aggregated medical outcome data is available.

2. The computer-implemented method of claim 1, wherein the graphical user interface comprises a first graphical user interface and wherein the method further comprises:
generating data for a second graphical user interface that when displayed on the display device displays data indicative of a clinical visit summary that chronicles one or more visits of the patient over a period of time.

3. The computer-implemented method of claim 2, wherein the clinical visit summary comprises one or more visual representations of one or more dates of patient visits for the patient.

4. The computer-implemented method of claim 2, wherein the clinical visit summary further comprises a diagram of one or more areas of a body of the patient in which the patient has received treatment.

5. The computer-implemented method of claim 1, further comprising:
receiving a request for the patient portal for the patient; and
identifying, from the request, an identity of the patient.

6. The computer-implemented method of claim 5, wherein a user who submits the request differs from the patient.

7. The computer-implemented method of claim 5, further comprising:
querying, at least partly based on the identity of patient, a data repository for medical data associated with the patient.

8. The computer-implemented method of claim 1, wherein the data for the graphical user interface is generated in real-time.

9. The computer-implemented method of claim 1, wherein the graphical user interface comprising one or more of: the first portion that specifies that the aggregated medical form data for the patient is viewable through the patient portal, with selection of the first portion causing a display of the aggregated medical form data when the aggregated medical form data is available; the second portion that specifies that the aggregated medical education data for the patient is viewable through the patient portal, with selection of the second portion causing a display of the aggregated medical education data when the aggregated medical education data is available; and the third portion that specifies that the aggregated medical outcome data for the patient is viewable through the patient portal, with selection of the third portion causing a display of the aggregated medical outcome data when the aggregated medical outcome data is available comprises:
the graphical user interface comprising the first portion that specifies that the aggregated medical form data for the patient is viewable through the patient portal, with selection of the first portion causing a display of the aggregated medical form data when the aggregated medical form data is available.

10. The computer-implemented method of claim 1, wherein the graphical user interface comprising one or more of: the first portion that specifies that the aggregated medical form data for the patient is viewable through the patient portal, with selection of the first portion causing a display of the aggregated medical form data when the aggregated medical form data is available; the second portion that specifies that the aggregated medical education data for the patient is viewable through the patient portal, with selection of the second portion causing a display of the aggregated medical education data when the aggregated medical education data is available; and the third portion that specifies that the aggregated medical outcome data for the patient is viewable through the patient portal, with selection of the third portion causing a display of the aggregated medical outcome data when the aggregated medical outcome data is available comprises:
the graphical user interface comprising the second portion that specifies that the aggregated medical education data for the patient is viewable through the patient portal, with selection of the second portion causing a display of the aggregated medical education data when the aggregated medical education data is available.

11. The computer-implemented method of claim 1, wherein the graphical user interface comprising one or more of: the first portion that specifies that the aggregated medical form data for the patient is viewable through the patient portal, with selection of the first portion causing a display of the aggregated medical form data when the aggregated medical form data is available; the second portion that specifies that the aggregated medical education data for the patient is viewable through the patient portal, with selection of the second portion causing a display of the aggregated medical education data when the aggregated medical education data is available; and the third portion that specifies that the aggregated medical outcome data for the patient is viewable through the patient portal, with selection of the third portion causing a display of the aggregated medical outcome data when the aggregated medical outcome data is available comprises:
the graphical user interface comprising the third portion that specifies that the aggregated medical outcome data for the patient is viewable through the patient portal, with selection of the third portion causing a display of the aggregated medical outcome data when the aggregated medical outcome data is available comprises.

12. A computer-implemented method comprising:
retrieving, from a data repository, aggregated medical form data for a patient, aggregated medical education data for the patient and aggregated medical outcome data for the patient;
wherein each of the aggregated medical form data for the patient, aggregated medical education data for the patient and aggregated medical outcome data for the patient is based on medical data that is received from a plurality of contributing organizations and is aggregated; and
generating data for a graphical user interface that when rendered on a display device renders a visual representation of a patient portal, with the graphical user interface comprising one or more of:
a first portion that specifies that the aggregated medical form data for the patient is viewable through the patient portal, with selection of the first portion causing a display of the aggregated medical form data when the aggregated medical form data is available;
a second portion that specifies that the aggregated medical education data for the patient is viewable through the patient portal, with selection of the second portion causing a display of the aggregated medical education data when the aggregated medical education data is available; and
a third portion that specifies that the aggregated medical outcome data for the patient is viewable through the patient portal, with selection of the third portion causing a display of the aggregated medical outcome data when the aggregated medical outcome data is available.

13. The computer-implemented method of claim 12, wherein at least one of the aggregated medical form data for the patient, the aggregated medical education data for the patient and the aggregated medical outcome data is medical data received from one of the contributing organizations.

14. The computer-implemented method of claim 12, further comprising:
receiving a request for the patient portal for the patient; and
identifying, from the request, an identity of the patient.

15. The computer-implemented method of claim 14, wherein a user who submits the request differs from the patient.

16. The computer-implemented method of claim 14, wherein the data repository comprises a first data repository, and wherein the method further comprises:
querying, at least partly based on the identity of the patient, a second data repository for medical data associated with the patient.

17. The computer-implemented method of claim 12, wherein the data for the graphical user interface is generated in real-time.

18. The computer-implemented method of claim 14, wherein the data for the graphical user interface is generated in real-time.

19. One or more machine-readable hardware storage devices storing instructions that are executable by one or more processing devices to perform operations comprising:
retrieving, from a data repository, aggregated medical form data for a patient, aggregated medical education data for the patient and aggregated medical outcome data for the patient;
wherein each of the aggregated medical form data for the patient, aggregated medical education data for the patient and aggregated medical outcome data for the patient is based on medical data that is received from a plurality of contributing organizations and is aggregated; and
generating data for a graphical user interface that when rendered on a display device renders a visual representation of a patient portal, with the graphical user interface comprising one or more of:
a first portion that specifies that the aggregated medical form data for the patient is viewable through the patient portal, with selection of the first portion causing a display of the aggregated medical form data when the aggregated medical form data is available;
a second portion that specifies that the aggregated medical education data for the patient is viewable through the patient portal, with selection of the second portion causing a display of the aggregated medical education data when the aggregated medical education data is available; and
a third portion that specifies that the aggregated medical outcome data for the patient is viewable through the patient portal, with selection of the third portion causing a display of the aggregated medical outcome data when the aggregated medical outcome data is available.

20. The one or more machine-readable hardware storage devices of claim 19, wherein at least one of the aggregated medical form data for the patient, the aggregated medical education data for the patient and the aggregated medical outcome data is medical data received from one of the contributing organizations.

21. The one or more machine-readable hardware storage devices of claim 19, wherein the operations further comprise:
receiving a request for the patient portal for the patient; and
identifying, from the request, an identity of the patient.

22. The one or more machine-readable hardware storage devices of claim 21, wherein a user who submits the request differs from the patient.

23. The one or more machine-readable hardware storage devices of claim 21, wherein the data repository comprises a first data repository, and wherein the operations further comprise:
querying, at least partly based on the identity of the patient, a second data repository for medical data associated with the patient.

24. An electronic system comprising:
one or more processing devices; and
one or more machine-readable hardware storage devices storing instructions that are executable by the one or more processing devices to perform operations comprising:
retrieving, from a data repository, aggregated medical form data for a patient, aggregated medical education data for the patient and aggregated medical outcome data for the patient;
wherein each of the aggregated medical form data for the patient, aggregated medical education data for the patient and aggregated medical outcome data for the patient is based on medical data that is received from a plurality of contributing organizations and is aggregated; and
generating data for a graphical user interface that when rendered on a display device renders a visual representation of a patient portal, with the graphical user interface comprising one or more of:
a first portion that specifies that the aggregated medical form data for the patient is viewable through the patient portal, with selection of the first portion causing a display of the aggregated medical form data when the aggregated medical form data is available;

a second portion that specifies that the aggregated medical education data for the patient is viewable through the patient portal, with selection of the second portion causing a display of the aggregated medical education data when the aggregated medical education data is available; and a third portion that specifies that the aggregated medical outcome data for the patient is viewable through the patient portal, with selection of the third portion causing a display of the aggregated medical outcome data when the aggregated medical outcome data is available.

25. The electronic system of claim 24, wherein at least one of the aggregated medical form data for the patient, the aggregated medical education data for the patient and the aggregated medical outcome data is medical data received from one of the contributing organizations.

26. The electronic system of claim 24, wherein the operations further comprise:

receiving a request for the patient portal for the patient; and identifying, from the request, an identity of the patient.

27. The electronic system of claim 26, wherein a user who submits the request differs from the patient.

28. The electronic system of claim 26, wherein the data repository comprises a first data repository, and wherein the operations further comprise:

querying, at least partly based on the identity of the patient, a second data repository for medical data associated with the patient.

29. The electronic system of claim 24, wherein the data for the graphical user interface is generated in real-time.

* * * * *

UNITED STATES PATENT AND TRADEMARK OFFICE
CERTIFICATE OF CORRECTION

| | | |
|---|---|---|
| PATENT NO. | : 8,762,170 B2 | Page 1 of 1 |
| APPLICATION NO. | : 14/104349 | |
| DATED | : June 24, 2014 | |
| INVENTOR(S) | : Ali Adel Hussam | |

It is certified that error appears in the above-identified patent and that said Letters Patent is hereby corrected as shown below:

On the Title Page, item (57) Col. 2, line 1, after "computer-implemented" insert -- method --

In the Claims

Col. 13, line 58, in claim 7, after "of" insert -- the --

Col. 14, line 67, in claim 11, delete "comprises" after "medical outcome data is available"

Signed and Sealed this
Twenty-fifth Day of November, 2014

Michelle K. Lee
*Deputy Director of the United States Patent and Trademark Office*